United States Patent
Larsson

(10) Patent No.: US 8,545,467 B2
(45) Date of Patent: Oct. 1, 2013

(54) WOUND COVER CONNECTING DEVICE

(75) Inventor: Michael Larsson, Zug (CH)

(73) Assignee: Medela Holding AG, Baar (CH)

( * ) Notice: Subject to any disclaimer, the term of this patent is extended or adjusted under 35 U.S.C. 154(b) by 529 days.

(21) Appl. No.: 12/741,868

(22) PCT Filed: Dec. 2, 2008

(86) PCT No.: PCT/CH2008/000505
§ 371 (c)(1),
(2), (4) Date: May 7, 2010

(87) PCT Pub. No.: WO2009/070905
PCT Pub. Date: Jun. 11, 2009

(65) Prior Publication Data
US 2010/0228206 A1    Sep. 9, 2010

(30) Foreign Application Priority Data

Dec. 7, 2007  (CH) ........................... 1900/07

(51) Int. Cl.
*A61M 1/00*  (2006.01)
(52) U.S. Cl.
USPC ............ 604/319; 604/317; 604/540; 604/543
(58) Field of Classification Search
USPC ................. 604/304–308, 313–316, 317–321, 604/540–543; 602/13; 128/887
See application file for complete search history.

(56) References Cited

U.S. PATENT DOCUMENTS

| | | | |
|---|---|---|---|
| 6,340,354 B1 | 1/2002 | Rambin | |
| 7,216,651 B2 | 5/2007 | Argenta et al. | |
| 2003/0040687 A1 | 2/2003 | Boynton et al. | |
| 2005/0085795 A1 | 4/2005 | Lockwood et al. | |
| 2005/0131327 A1* | 6/2005 | Lockwood et al. | 602/41 |
| 2005/0137539 A1 | 6/2005 | Biggie et al. | |
| 2007/0021698 A1 | 1/2007 | Fleischmann | |
| 2007/0032778 A1 | 2/2007 | Heaton et al. | |
| 2007/0129660 A1 | 6/2007 | McLeod et al. | |
| 2007/0265586 A1 | 11/2007 | Joshi et al. | |

FOREIGN PATENT DOCUMENTS

| | | |
|---|---|---|
| EP | 1772160 | 4/2007 |
| EP | 1884223 | 2/2008 |
| JP | 2005-334188 | 12/2005 |
| JP | 2006-116162 | 5/2006 |

(Continued)

OTHER PUBLICATIONS

Swiss Search Report for corresponding Swiss Patent Application No. 1900/07, dated Jul. 14, 2008.

(Continued)

*Primary Examiner* — Tatyana Zalukaeva
*Assistant Examiner* — Benedict L Hanrahan
(74) *Attorney, Agent, or Firm* — McDonnell Boehnen Hulbert & Berghoff LLP

(57) ABSTRACT

A wound cover connecting device for the sealing connection of a drainage tube and a wound cover covering a wound has a base body for the sealing contact on an outside of the cover. According to the invention, the device comprises at least one penetration element for producing a through-passage in the cover. The device enables a simple, fast, and tight connection between the cover and the tube. In addition, it enables a treatment of the wound that is as uniform and has as large a surface as possible.

14 Claims, 4 Drawing Sheets

(56) References Cited

FOREIGN PATENT DOCUMENTS

| WO | 01/34223 | 5/2001 |
|----|----------|--------|
| WO | 03/018098 | 3/2003 |
| WO | 03/073970 | 9/2003 |
| WO | 2005/025447 | 3/2005 |
| WO | 2006/012992 | 2/2006 |
| WO | 2006/105892 | 10/2006 |
| WO | 2007/084792 | 7/2007 |
| WO | 2007/143060 | 12/2007 |

OTHER PUBLICATIONS

International Preliminary Report on Patentability and Written Opinion for corresponding PCT Application No. PCT/CH2008/000505, dated Jul. 15, 2010.

International Search Report for corresponding International Patent App. No. PCT/CH2008/000505 dated May 19, 2009.

* cited by examiner

WOUND COVER CONNECTING DEVICE

CROSS REFERENCE TO RELATED APPLICATIONS

The present application claims priority to International Application No. PCT/CH/2008/000505 filed on Dec. 2, 2008, which claims priority to Switzerland Patent Application No. 01900/07 filed on Dec. 7, 2007.

TECHNICAL FIELD

The invention relates to a wound cover connecting device.

PRIOR ART

It is known to treat large or poorly healing wounds using a vacuum drainage unit. The wound is in this case covered with a cover, for example a film or a stiff cap, such that a wound space is obtained. A drainage tube is introduced into the wound space from the outside and is connected to a vacuum pump in order to suck wound secretions from the wound. A wound dressing is usually placed on the wound under the cover in order to fill the wound space and, in particular, in order to distribute the vacuum uniformly across the wound surface.

At its end toward the wound, the drainage tube is preferably designed such that the vacuum can be applied in a distributed manner. For example, US 2005/0137539 discloses an elongate tube end with perforations.

JP 2006116162 discloses a simplified wound drainage system without an absorption pad in the wound, but with a transparent cover that is stiff enough not to touch the bottom of the wound bed. The drainage tube has an end that passes through the wound cover, and it is provided with several holes in an end area.

WO 2006/105892 describes a connecting device or suction head for connecting the tube and cover, wherein this connecting element is arranged under the cover and protrudes from the latter only with one attachment piece. The connecting element has radially arranged channels through which suction can be effected.

In JP 2005334188, a hollow frame with perforations is present, which is connected to the suction source.

WO 01/34223 proposes using a flat, round suction head, which has a centrally arranged suction opening and, distributed around this opening, protuberances directed toward the wound bed.

In US 2007/0032778 too, the suction head has protuberances extending into the wound bed.

In the examples described above, the suction head is in each case located in the wound bed underneath the cover. The same applies to WO 2007/084792, US 2007/0129660, EP 1 772 160 and U.S. Pat. No. 7,216,651.

In WO 03/018098, the tube is introduced into a connector piece, which adheres to the top of the cover.

The known types of connections have a number of disadvantages. Creating the connection is in most cases time-consuming and requires a certain degree of skill. There is often a danger of the connection not being tight. Moreover, the connection elements or suction heads according to the prior art either cannot provide suction distributed uniformly across the wound area or they are relatively large and take up a lot of space in the wound bed. In the latter case, there is a danger that they come into contact with the bottom of the wound bed and cause the patient unnecessary pain or have a negative effect on the wound healing process.

DISCLOSURE OF THE INVENTION

It is therefore an object of the invention to make available a wound cover connecting device with which a tight connection between a tube and a wound cover can be easily established and which allows a line to be routed into the wound in a short time.

The wound cover connecting device according to the invention, for sealingly connecting a tube and a wound cover closing a wound, has a main body for bearing sealingly on an outside of the cover. According to the invention, the device has at least one penetration element for creating a through-opening in the cover.

The wound cover connecting device according to the invention is therefore a coupling part or attachment part for the connection of wound cover and tube. It thus forms an interface.

The tube can be, but does not have to be, a drainage tube for aspirating wound secretions. It can equally be a tube that delivers a gas or a liquid to the wound bed. The connecting device thus serves in the first instance for connection to a suction tube for applying a vacuum to the wound. However, alternatively or in addition to this, it can also serve to deliver medicaments, liquids or gases to the wound.

In a preferred embodiment, the at least one penetration element has a sharp-pointed and/or cutting shape.

In one embodiment, the at least one penetration element serves only to create a connecting channel between wound bed and tube. The penetration element is preferably hollow and is provided with at least one through-opening, such that the suction action or the delivery of liquids or gases can take place through this penetration element.

In a preferred embodiment, the connecting device is designed as a separate part that can be connected to a drainage tube. In particular, the tube is able to be pushed onto this part. In another likewise preferred embodiment, the connecting device is an integral component part of the drainage tube.

By virtue of the device according to the invention, the wound can be covered in a first step. Routing the line to the wound, i.e. connecting the wound cover to the tube, can take place in a second and separate step.

In order to route the line, the device according to the invention simply has to be placed on the cover and the at least one penetration element pushed through the cover. In a preferred embodiment, this piercing is achieved simply by means of the device being placed with sufficient pressure onto the cover. If the penetration elements have a blunt shape, the pressure has to be higher than if they have a sharp-pointed or cutting shape.

Since no parts have to be introduced subsequently under the cover, the danger of the walls of the wound being touched or disturbed is relatively low. The line is therefore routed in a way that causes the patient much less pain than in the known devices. Moreover, the wound can also be covered in this way in the operating theater, the patient taken out of theater, and the line inserted only in the postoperative care unit. This also causes the patient less pain, since the personnel in the postoperative care unit are able to take more time and since the patient does not have to be moved with a tube already attached.

It is also advantageous that the device is able to be used with a very wide variety of wound closures. The device is also inexpensive to produce.

It is a further object of the invention to make available a wound cover connecting device that allows the largest possible wound area to be acted on at the same time.

For this purpose the device according to the invention has several penetration elements, which are spaced apart from one another and which are designed to pierce through the cover at a plurality of locations spaced apart from one another.

These penetration elements are preferably arranged uniformly across the entire surface area of the main body.

Other advantageous embodiments are set forth in the dependent claims.

BRIEF DESCRIPTION OF THE DRAWINGS

The subject matter of the invention is explained in detail below with reference to preferred illustrative embodiments depicted in the attached drawings, in which.

DETAILED DESCRIPTION

Figure 1:
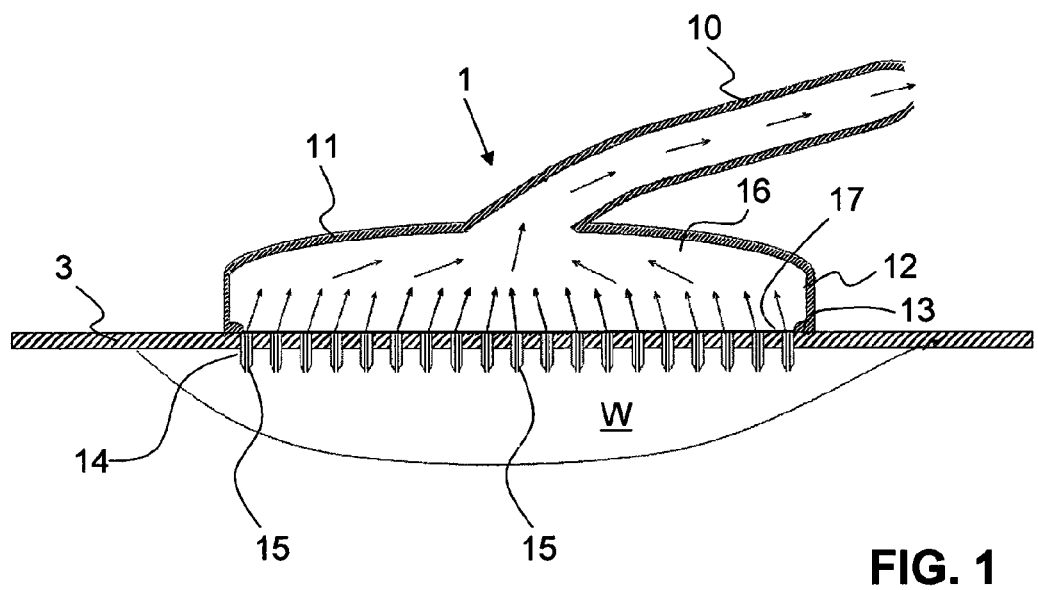
FIG. 1 shows a longitudinal section through a schematic representation of a wound cover connecting device according to a first embodiment of the invention when in use.

FIG. 1 shows a longitudinal section through a wound with a wound bed W, which is covered in an airtight manner by a wound cover 3. The wound cover 3 is preferably secured on the healthy skin surrounding the wound, in particular with an adhesive tape. The wound cover 3 can be in the form of known wound covers, in particular films or stiff caps. The wound bed W can be left naturally or can be filled with a wound dressing, in particular a foam or another wound filler of a known type.

To promote healing, the wound is treated using a vacuum. For this purpose, a suction line leading from a suction source, in particular from a vacuum pump, is routed through the cover 3 into the wound space. However, for this purpose, and in contrast to the prior art, an endpiece of a suction tube is not inserted through the wound cover 3 into the wound space, and instead the connecting device 1 according to the invention simply has to be placed on the wound cover 3 and pressed onto the latter.

This connecting device 1 has a main body 11, on one side of which a hollow attachment piece 10 is integrally formed. On another side, preferably the opposite side, the main body 11 has a contact wall 17, which is provided with penetration elements 14.

The main body 11 has a surface area that is preferably many times greater than the cross-sectional area of the attachment piece 10. The main body 11 is preferably rigid and dimensionally stable. It is made in particular of metal or plastic. It is preferably formed integrally with the attachment piece 10.

Figure 4:
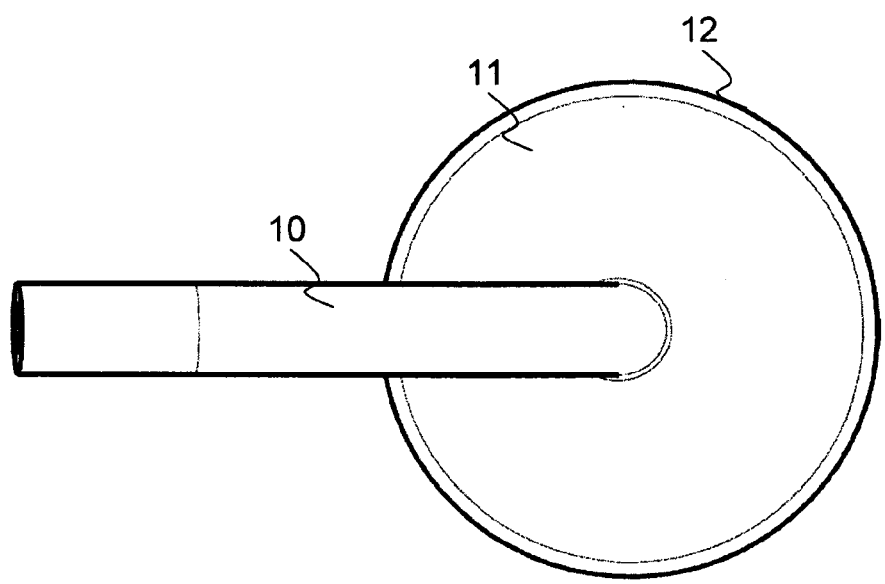
FIG. 4 shows a top view of the device according to FIG. 2.

The main body 11 is preferably round in cross section and in a plan view, as can be seen in FIG. 4, for example. However, it can also be rectangular, oval, star-shaped or of another shape. It is preferably relatively flat. Its outer shape can correspond, for example, to a shower head, such that its longitudinal section has roughly a rectangular shape. However, the main body 11 can also be approximately hemispherical, frustoconical or pyramid-shaped, such that its longitudinal section has approximately the shape of a semicircle or triangle.

Figure 3:
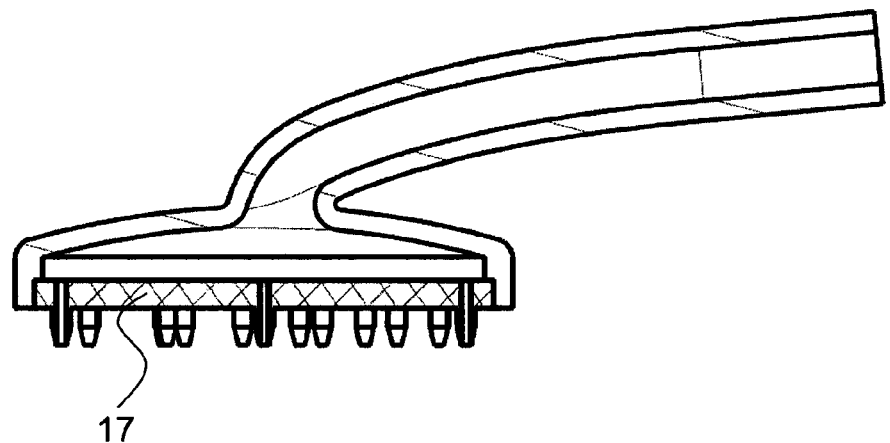
FIG. 3 shows a longitudinal section through the device according to FIG. 2.

The main body 11 is designed open at the bottom, i.e. toward the wound, and is closed by the contact wall 17. In this way, at least one hollow space 16 is formed in the interior of the main body 11. It is also possible to have a plurality of hollow spaces or through-channels that communicate with one another or are separate from one another. The at least one hollow space 16 is connected to the channel of the attachment piece 10. This can be seen in FIGS. 1 and 3.

The attachment piece 10 is preferably made from the same material as the main body 11, in particular from metal or plastic. It can be arranged laterally on the main body 11, i.e. on the jacket 12 of the main body 11, or can be attached to the upper face of the main body 11 directed away from the wound bed. In the latter case, it can additionally protrude perpendicularly from this face or, as is shown in the figures, extend not perpendicularly thereto.

The attachment piece 10 can be designed as a short tubular component onto or into which a drainage tube can be plugged. The attachment piece 10, however, can also be designed integrally with the drainage tube. In the latter case, the connecting device according to the invention forms the wound-side end of the drainage tube. The drainage tube is preferably made of silicone. Its end, however, can be made of another material.

On the wound side, the main body 11 is provided with a sealing element, in particular a sealing ring 13 or sealing surface extending around the jacket 12. The main body 11 lies with the jacket 12 on the wound cover 3, and the sealing ring 13 forms an airtight connection. Instead of or in addition to the sealing ring 13, the main body 11 can also be sealed off with respect to the cover 3 by known means, for example it can be affixed with an adhesive tape.

As is shown in FIG. 1, the sealing ring 13 can be arranged on the inner face of the main body 11 or of the jacket 12. However, it can be arranged alternatively or in addition on the outer face or end face of the jacket 12. The sealing element 13 is preferably self-adherent, in particular adhesive, with respect to the cover 3.

The contact wall 17 and the penetration elements 14 are arranged inside the sealing surface of the main body 11, in other words inside the sealing element 13.

The contact wall 17 closes off the hollow space 16 of the main body on the side toward the wound. This contact wall 17 is preferably formed by a membrane or a flexible wall that is connected in an airtight manner to the jacket 12 of the main body 11. It is preferably flush with the lower end face of the jacket 12 or of the sealing element 13. However, it can also be set back from the latter or in front of it.

The contact wall 17 is so flexible that it adapts to the surface of the cover 3 and preferably bears across approximately its entire surface area on the cover 3.

Figure 2:
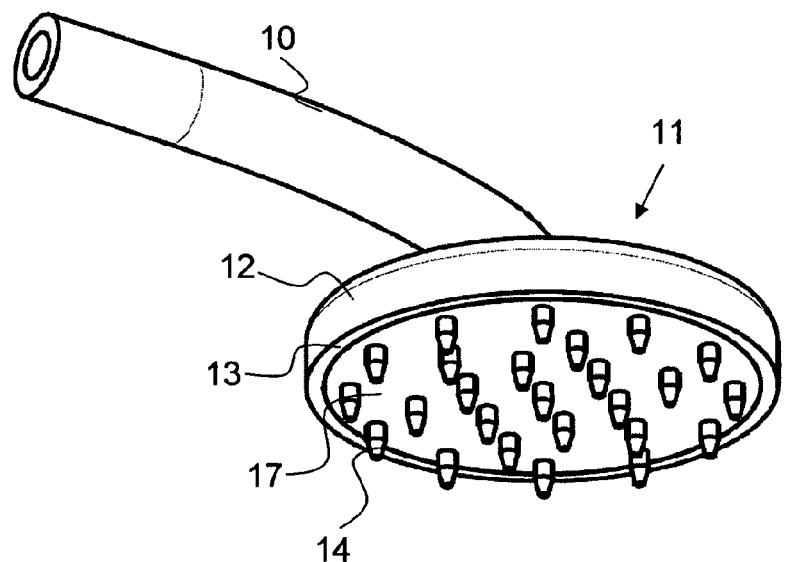
FIG. 2 shows a perspective view of the device according to the first embodiment.
Figure 5:
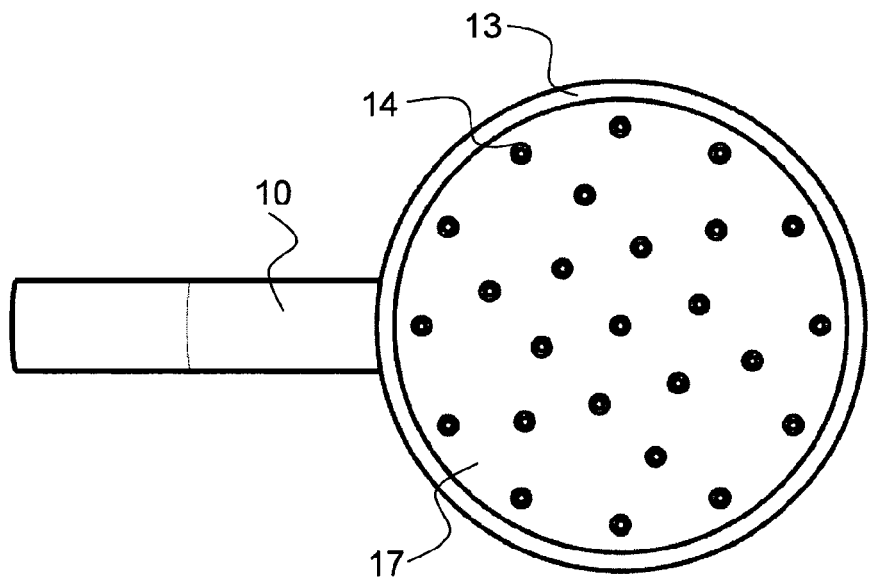
FIG. 5 shows a bottom view of the device according to FIG. 2.

The contact wall 17 has at least one piercing or penetration element 14. In this example, several penetration elements 14 are present. These penetration elements 14 are preferably distributed across the entire surface of the contact wall 17, as can be seen from FIGS. 2 and 5, for example. They are preferably distributed in a uniform manner.

Figure 6:
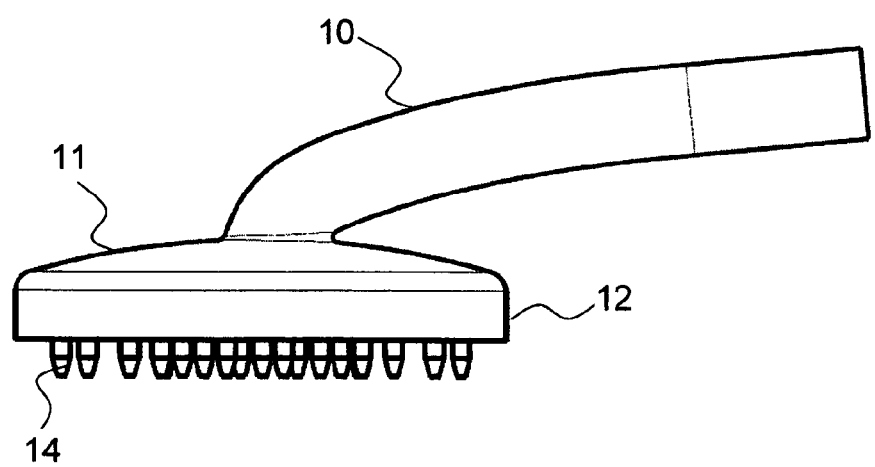
FIG. 6 shows a side view of the device according to FIG. 2.

These penetration elements 14 protrude from the lower end face of the main body 11 and the contact wall 17 and extend toward the wound. This can be seen from FIG. 6, for example.

If the connecting device 1 according to the invention is now placed onto the cover 3 and pressed gently onto the cover 3, the penetration elements 14 pierce through or penetrate this cover 3 and generate through-openings in the cover. In this way, continuous channels are created between the hollow space 16 or drainage tube and the wound bed W. This can be seen in FIG. 1. The membrane 17 preferably nestles onto the surface of the wound cover 3.

The penetration elements 14 are preferably pins or tubes, in particular of metal or plastic. They preferably have a conical or pyramid-like basic shape. They preferably have a sharp-pointed and/or cutting shape.

In the example shown here, the penetration elements 14 have through-channels 15. All the penetration elements 14 can be provided with channels 15, although they do not all have to be provided with them. The elements 14 are designed in particular as hollow needles, such that the connection between the hollow space 16 or drainage tube and the wound bed W is through these channels 15.

FIG. 1 illustrates the use of the device as a wound drainage suction head. The attachment piece 10 is connected to a suction tube (not shown) of a suction source. The wound fluid is now sucked through the through-channels 15 into the suction space or hollow space 16 and from there via the attachment piece 10 into the suction tube. The direction is indicated by arrows.

However, the device according to FIG. 1 could also be used in the reverse direction, i.e. a gas or a liquid could also be introduced through the needles 15 into the wound W.

Typical dimensions of such a device are:

| | |
|---|---|
| diameter of the main body 11: | 20 to 40 mm; |
| height of the main body: | about 5 mm; |
| external diameter of a penetration element 14: | 1 to 2 mm; |
| height of the penetration element 14: | 0.2 to 5 mm; |
| internal diameter of a channel 15: | 0.5 mm to 1 mm. |

Figure 7:
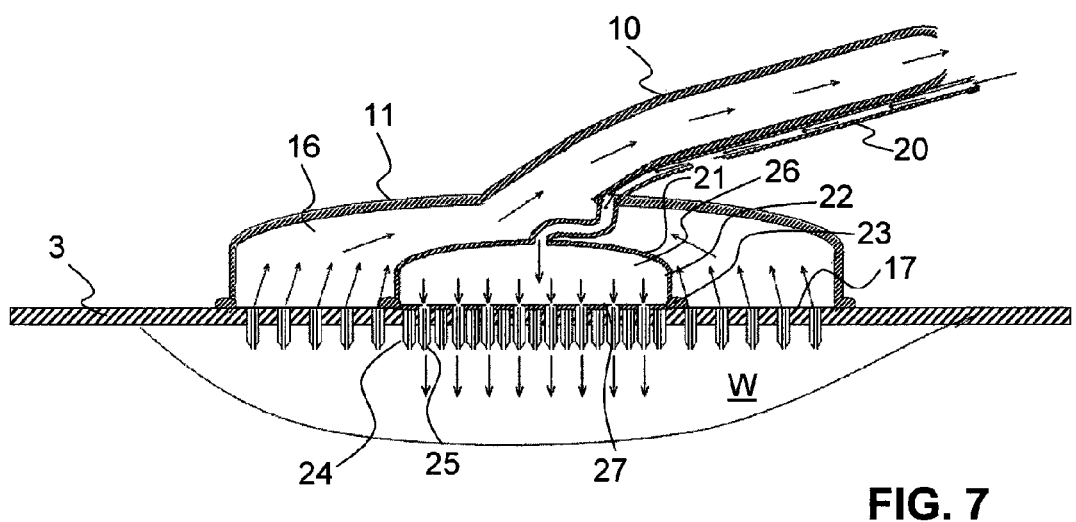
FIG. 7 shows a longitudinal section through a schematic representation of a wound cover connecting device according to a second embodiment of the invention when in use.

FIG. 7 shows a multipurpose head. The basic structure is the same as in the preceding example, such that identical parts are designated by the same reference signs. In the interior of the first main body 11, however, there is now a second main body 21 with a smaller surface area. This is also adjoined by a second attachment piece 20, which extends outside and adjacent to the first attachment piece 10. It could also extend at a distance from the latter or in the interior thereof.

Like the first main body, the second main body 21 can be round, oval, rectangular, star-shaped or have another basic shape. Its surface area is preferably also many times greater than the cross-sectional area of its attachment piece or of the connected drainage tube. The second main body 21 is here arranged centrally in the first main body 11. However, it can also be arranged peripherally or on the outside, adjoining the first main body or at a distance from it. It once again preferably has a sealing element 23, preferably a sealing ring or a sealing surface, that extends around its jacket 22. This sealing element 23 is also preferably self-adherent with respect to the cover.

The second main body 21 is likewise preferably rigid or dimensionally stable. It is likewise open at the bottom toward the wound and is closed by a contact wall 27, in particular an elastic membrane, that adapts in shape to the wound cover 3. This contact wall 27 is also provided with penetration elements 24, in particular hollow needles. These penetration elements 24 preferably also have a sharp-pointed and/or cutting shape. Their dimensions can be the same as or greater or smaller than those of the first-mentioned penetration elements 14. In particular, their through-channels 25 can have the same internal diameter as, or a greater or smaller internal diameter than, the through-channels 15 of the first penetration elements 14.

As is shown in FIG. 7, the wound fluid can thus be aspirated from the wound bed through the first needles 15 and, without changing the position of the device according to the invention, a medicament, a liquid or a gas can be delivered to the wound bed via the second needles 25. This delivery can take place at the same time as the suction or at a different time. However, different substances can also be delivered to the wound bed through both needles. Moreover, the delivery can take place through the first needles 15 and the suction via the second needles 25. It is also possible for one or more further main bodies to be present with further needles, which are arranged outside the first main body or in the latter. In FIG. 7, the sealing elements 13, 23 extend outside the respective main bodies 11, 21. However, alternatively or in addition to this, they can also once again extend under or inside the main bodies 11, 21.

The device according to the invention permits simple, quick and leaktight connection of the cover to a tube. It also permits wound treatment that is as uniform as possible and that covers as large a surface area as possible.

The invention claimed is:

1. A wound cover connecting device for sealingly connecting a drainage tube and a wound cover closing a wound, wherein the device has a main body for bearing sealingly on an outer face of the wound cover, the main body having a lower end face, wherein the connection device has a sealing element extending around the main body, the sealing element being able to seal the main body against the wound cover while the main body is resting with its lower end face on the wound cover, wherein the device has at least one penetration element for creating a through-opening in the wound cover, wherein the at least one penetration element has a shape that is at least one of sharp-pointed or cutting, and wherein the at least one penetration element protrudes from the lower end face of the main body and wherein the main body, on the wound side, is closed by a contact wall, and wherein the at least one penetration element is arranged in the contact wall.

2. The device as claimed in claim 1, comprising a plurality of said penetration elements spaced apart from one another and designed to pierce through the cover at a plurality of locations spaced apart from one another.

3. The device as claimed in claim 1, wherein the penetration element is arranged inside a sealing contact area of the main body.

4. The device as claimed in claim 1, wherein the penetration element has a through-channel for aspirating the liquid.

5. The device as claimed in claim 1, wherein the sealing element is self-adhesive.

6. The device as claimed in claim 1, wherein the sealing element extends on the outer face and/or inner face of the main body.

7. The device as claimed in claim 1, wherein the device has an attachment piece for connection to a suction source, and wherein the main body has a surface area greater than the cross-sectional area of the attachment piece.

8. The device as claimed in claim 1, wherein the main body has a substantially round or oval surface area.

9. The device as claimed in claim 1, wherein the contact wall is designed to adapt automatically to the surface of the cover.

10. The device as claimed in claim 9, wherein the contact wall is elastic.

11. The device as claimed in claim 1, wherein the penetration element is distributed approximately uniformly across the entire contact wall of the main body.

12. The device as claimed in claim 1, wherein the device has at least one second main body with a second penetration element.

13. The device as claimed in claim 12, wherein the at least one second main body is arranged in the first main body.

14. The device as claimed in claim 12, wherein the at least one second main body has a sealing element for bearing sealingly on the cover of the wound.

* * * * *